United States Patent
Sattiraju et al.

(10) Patent No.: US 10,284,923 B2
(45) Date of Patent: May 7, 2019

(54) LOW POWER RADIOFREQUENCY (RF) COMMUNICATION SYSTEMS FOR SECURE WIRELESS PATCH INITIALIZATION AND METHODS OF USE

(71) Applicant: LIFESIGNALS, INC., Fremont, CA (US)

(72) Inventors: Venkateswara Rao Sattiraju, Union City, CA (US); Ali Niknejad, Berkeley, CA (US); Louis Yun, Los Altos, CA (US)

(73) Assignee: LIFESIGNALS, INC., Fremont, CA (US)

( * ) Notice: Subject to any disclaimer, the term of this patent is extended or adjusted under 35 U.S.C. 154(b) by 0 days.

(21) Appl. No.: 14/845,175

(22) Filed: Sep. 3, 2015

(65) Prior Publication Data

US 2016/0134950 A1    May 12, 2016

Related U.S. Application Data

(63) Continuation of application No. 12/739,549, filed as application No. PCT/US2008/080716 on Oct. 22, 2008, now abandoned.
(Continued)

(51) Int. Cl.
*A61B 5/00* (2006.01)
*A61B 5/05* (2006.01)
(Continued)

(52) U.S. Cl.
CPC .......... *H04Q 9/00* (2013.01); *H04L 63/0428* (2013.01); *H04W 12/02* (2013.01); *H04W 52/50* (2013.01);
(Continued)

(58) Field of Classification Search
CPC ....... H04Q 9/00; H04L 63/0428; H04L 29/06; H04W 52/50
(Continued)

(56) References Cited

U.S. PATENT DOCUMENTS

| 4,313,443 | A | 2/1982 | Frosch et al. |
| 4,784,162 | A | 11/1988 | Ricks et al. |

(Continued)

FOREIGN PATENT DOCUMENTS

| EP | 1070479 A2 | 1/2001 |
| EP | 1292218 B1 | 4/2006 |

(Continued)

OTHER PUBLICATIONS

Berrou, et al. Near Shannon limit error-correcting coding and decoding: Turbo-codes. 1. IEEE Int. Conf. Commun., vol. 2, Geneva, Switzerland, May 1993, p. 1064-1070.
(Continued)

*Primary Examiner* — Alexander Lagor
(74) *Attorney, Agent, or Firm* — Wilson Sonsini Goodrich & Rosati

(57) ABSTRACT

Provided herein is a wireless healthcare system comprising at least one sensor and a base unit adaptable to be in communication with the sensor. The sensor can be is adaptable to communicate with the base unit at a first power during formation of a communication link and is further adaptable to communicate with the base unit at a second power after the communication link has been formed, and wherein the sensor and base unit are components of a wireless healthcare system. The sensor can be a patch adaptable to be positioned on the surface of a patient. Further provided herein is a method of using the wireless healthcare system and kit.

23 Claims, 2 Drawing Sheets

Related U.S. Application Data

(60) Provisional application No. 60/982,225, filed on Oct. 24, 2007.

(51) Int. Cl.

| | | |
|---|---|---|
| *H04L 9/00* | (2006.01) | |
| *H04L 9/08* | (2006.01) | |
| *H04Q 9/00* | (2006.01) | |
| *H04L 29/06* | (2006.01) | |
| *H04W 12/02* | (2009.01) | |
| *H04W 52/50* | (2009.01) | |

(52) U.S. Cl.
CPC .... *A61M 2205/3592* (2013.01); *H04L 63/061* (2013.01); *H04Q 2209/40* (2013.01); *H04Q 2209/47* (2013.01)

(58) Field of Classification Search
USPC ......... 713/168–174, 182–186, 202; 709/206, 709/225, 229, 249, 389; 726/2–8
See application file for complete search history.

(56) References Cited

U.S. PATENT DOCUMENTS

| | | |
|---|---|---|
| 5,124,128 A | 6/1992 | Hildenbrand et al. |
| 5,231,990 A | 8/1993 | Gauglitz |
| 5,511,553 A | 4/1996 | Segalowitz |
| 5,519,827 A | 5/1996 | Mizushima |
| 5,717,848 A | 2/1998 | Watanabe et al. |
| 5,718,234 A | 2/1998 | Warden et al. |
| 5,720,770 A | 2/1998 | Nappholz et al. |
| 5,913,727 A | 6/1999 | Ahdoot |
| 5,957,854 A | 9/1999 | Besson et al. |
| D439,981 S | 4/2001 | Kasabach et al. |
| 6,230,970 B1 | 5/2001 | Walsh et al. |
| 6,275,143 B1 | 8/2001 | Stobbe |
| 6,278,499 B1 | 8/2001 | Darbee et al. |
| 6,295,461 B1 | 9/2001 | Palmer et al. |
| D451,604 S | 12/2001 | Kasabach et al. |
| 6,336,900 B1 | 1/2002 | Alleckson et al. |
| D460,971 S | 7/2002 | Sica et al. |
| 6,436,058 B1 | 8/2002 | Krahner et al. |
| 6,454,708 B1 | 9/2002 | Ferguson et al. |
| 6,463,039 B1 | 10/2002 | Ricci et al. |
| 6,494,829 B1 | 12/2002 | New, Jr. et al. |
| 6,527,711 B1 | 3/2003 | Stivoric et al. |
| 6,546,121 B1 * | 4/2003 | Oda ................ G06K 9/00597 382/117 |
| 6,558,320 B1 | 5/2003 | Causey, III et al. |
| 6,595,929 B2 | 7/2003 | Stivoric et al. |
| 6,605,038 B1 | 8/2003 | Teller et al. |
| 6,677,852 B1 | 1/2004 | Landt |
| 6,694,180 B1 | 2/2004 | Boesen |
| 6,731,962 B1 | 5/2004 | Katarow et al. |
| 6,885,191 B1 | 4/2005 | Gleman |
| 6,893,396 B2 | 5/2005 | Schulze et al. |
| 6,909,420 B1 | 6/2005 | Nicolas et al. |
| 7,020,508 B2 | 3/2006 | Stivoric et al. |
| 7,103,578 B2 | 9/2006 | Beck et al. |
| 7,125,382 B2 | 10/2006 | Zhou et al. |
| 7,206,630 B1 | 4/2007 | Tarler |
| 7,270,633 B1 | 9/2007 | Goscha et al. |
| 7,277,547 B1 * | 10/2007 | Delker ................ H04L 63/0272 380/270 |
| 7,294,105 B1 * | 11/2007 | Islam .................. A61B 5/0006 128/903 |
| 7,376,234 B1 | 5/2008 | Gardiner |
| 7,382,247 B2 | 6/2008 | Welch et al. |
| 7,571,369 B2 | 8/2009 | Wang et al. |
| 7,602,301 B1 | 10/2009 | Stirling et al. |
| 7,603,255 B2 | 10/2009 | Case, Jr. et al. |
| 7,733,224 B2 | 6/2010 | Tran |
| 7,969,307 B2 | 6/2011 | Peeters |
| 8,201,099 B1 | 6/2012 | Osbourn et al. |
| 8,271,891 B1 | 9/2012 | Osbourn et al. |
| 8,611,319 B2 | 12/2013 | Magar et al. |
| 8,617,152 B2 | 12/2013 | Werneth et al. |
| 8,926,509 B2 | 1/2015 | Magar et al. |
| 9,046,919 B2 | 6/2015 | Niknejad |
| 9,155,469 B2 | 10/2015 | Magar et al. |
| 2001/0003163 A1 | 6/2001 | Bungert et al. |
| 2001/0047127 A1 | 11/2001 | New et al. |
| 2002/0019584 A1 * | 2/2002 | Schulze ............... G06F 19/3418 600/300 |
| 2002/0065828 A1 | 5/2002 | Goodspeed |
| 2002/0109621 A1 * | 8/2002 | Khair ................... A61B 5/0006 341/174 |
| 2003/0004403 A1 | 1/2003 | Drinan et al. |
| 2003/0139903 A1 | 7/2003 | Zweig et al. |
| 2003/0208113 A1 | 11/2003 | Mault et al. |
| 2003/0219035 A1 | 11/2003 | Schmidt |
| 2003/0236103 A1 | 12/2003 | Tamaki et al. |
| 2004/0013097 A1 | 1/2004 | Massa |
| 2004/0027385 A1 | 2/2004 | Rekimoto et al. |
| 2004/0077975 A1 | 4/2004 | Zimmerman |
| 2004/0199056 A1 | 10/2004 | Husemann et al. |
| 2004/0236192 A1 | 11/2004 | Necola Shehada et al. |
| 2005/0035852 A1 | 2/2005 | Paulsen |
| 2005/0090718 A1 | 4/2005 | Dodds |
| 2005/0101841 A9 | 5/2005 | Kaylor et al. |
| 2005/0113167 A1 | 5/2005 | Buchner et al. |
| 2005/0119533 A1 | 6/2005 | Sparks et al. |
| 2005/0197680 A1 | 9/2005 | DelMain et al. |
| 2005/0202782 A1 * | 9/2005 | Sasai ..................... H04W 48/16 455/41.2 |
| 2005/0206518 A1 | 9/2005 | Welch et al. |
| 2005/0227719 A1 * | 10/2005 | Gunaratnam ......... H04W 48/18 455/510 |
| 2005/0277841 A1 | 12/2005 | Shennib |
| 2005/0282633 A1 | 12/2005 | Nicolas et al. |
| 2006/0004303 A1 | 1/2006 | Weidenhaupt et al. |
| 2006/0025657 A1 | 2/2006 | Rosenfeld et al. |
| 2006/0031102 A1 | 2/2006 | Teller et al. |
| 2006/0056636 A1 * | 3/2006 | Schrum, Jr. .......... H04L 63/0428 380/273 |
| 2006/0103534 A1 * | 5/2006 | Arms ..................... E01F 13/12 340/572.1 |
| 2006/0106289 A1 | 5/2006 | Elser et al. |
| 2006/0122473 A1 | 6/2006 | Kill et al. |
| 2006/0122474 A1 | 6/2006 | Teller et al. |
| 2006/0136294 A1 | 6/2006 | Linden et al. |
| 2006/0154542 A1 | 7/2006 | Underwood et al. |
| 2006/0173259 A1 | 8/2006 | Flaherty et al. |
| 2006/0202816 A1 | 9/2006 | Crump et al. |
| 2006/0203083 A1 * | 9/2006 | Wilson, Jr. ............ H04N 7/148 348/14.02 |
| 2006/0224048 A1 | 10/2006 | Devaul et al. |
| 2006/0264767 A1 | 11/2006 | Shennib |
| 2007/0014409 A1 * | 1/2007 | Batra ..................... H04B 5/02 380/270 |
| 2007/0027388 A1 | 2/2007 | Chou |
| 2007/0061211 A1 | 3/2007 | Ramer et al. |
| 2007/0081505 A1 | 4/2007 | Roberts |
| 2007/0087780 A1 | 4/2007 | Nassimi |
| 2007/0097076 A1 | 5/2007 | Gross |
| 2007/0100218 A1 | 5/2007 | Sweitzer et al. |
| 2007/0100219 A1 | 5/2007 | Sweitzer et al. |
| 2007/0118038 A1 | 5/2007 | Bodecker et al. |
| 2007/0135866 A1 | 6/2007 | Baker et al. |
| 2007/0156450 A1 | 7/2007 | Roehm et al. |
| 2007/0162763 A1 | 7/2007 | Bender et al. |
| 2007/0208233 A1 | 9/2007 | Kovacs et al. |
| 2007/0208262 A1 | 9/2007 | Kovacs et al. |
| 2007/0232234 A1 | 10/2007 | Inzerillo et al. |
| 2007/0244383 A1 | 10/2007 | Talbot et al. |
| 2007/0270672 A1 | 11/2007 | Hayter |
| 2007/0271466 A1 | 11/2007 | Mak et al. |
| 2007/0279217 A1 | 12/2007 | Venkatraman et al. |
| 2007/0282218 A1 | 12/2007 | Yarden |
| 2007/0293781 A1 | 12/2007 | Sims et al. |
| 2008/0001735 A1 | 1/2008 | Tran |
| 2008/0021214 A1 | 1/2008 | Rao et al. |

(56) References Cited

U.S. PATENT DOCUMENTS

| | | |
|---|---|---|
| 2008/0046562 A1 | 2/2008 | Butler |
| 2008/0054880 A1* | 3/2008 | Miyauchi ............... G01R 15/08 |
| | | 324/76.29 |
| 2008/0065877 A1 | 3/2008 | Son et al. |
| 2008/0119707 A1 | 5/2008 | Stafford |
| 2008/0139894 A1 | 6/2008 | Szydlo-Moore et al. |
| 2008/0162475 A1 | 7/2008 | Meggs et al. |
| 2008/0252596 A1 | 10/2008 | Bell et al. |
| 2008/0281606 A1 | 11/2008 | Kitts et al. |
| 2008/0319774 A1 | 12/2008 | O'Sullivan et al. |
| 2009/0008151 A1 | 1/2009 | Turner et al. |
| 2009/0037670 A1* | 2/2009 | Rofougaran .......... G06F 13/385 |
| | | 711/154 |
| 2009/0044282 A1 | 2/2009 | Govindaraju |
| 2009/0051544 A1 | 2/2009 | Niknejad |
| 2009/0054737 A1* | 2/2009 | Magar .................. A61B 5/0205 |
| | | 600/300 |
| 2009/0106413 A1 | 4/2009 | Salo et al. |
| 2009/0164269 A1 | 6/2009 | Gupta et al. |
| 2009/0316618 A1 | 12/2009 | Fielding et al. |
| 2010/0013607 A1 | 1/2010 | Sabo et al. |
| 2010/0049006 A1 | 2/2010 | Magar et al. |
| 2010/0160746 A1 | 6/2010 | Venkatraman et al. |
| 2010/0316043 A1 | 12/2010 | Doi et al. |
| 2011/0019595 A1 | 1/2011 | Magar et al. |
| 2011/0019824 A1 | 1/2011 | Sattiraju et al. |
| 2012/0256492 A1 | 10/2012 | Song et al. |
| 2013/0123666 A1 | 5/2013 | Giuffrida et al. |
| 2014/0091947 A1 | 4/2014 | Magar et al. |
| 2015/0289814 A1 | 10/2015 | Magar et al. |

FOREIGN PATENT DOCUMENTS

| | | |
|---|---|---|
| GB | 2420628 A | 5/2006 |
| JP | 2006055530 A | 3/2006 |
| KR | 20040032451 A | 4/2004 |
| KR | 20040074056 A | 8/2004 |
| KR | 20050072558 A | 7/2005 |
| KR | 100653208 B1 | 11/2006 |
| KR | 20070048168 A | 5/2007 |
| WO | WO-8902682 A1 | 3/1989 |
| WO | WO-8904093 A1 | 5/1989 |
| WO | WO-8904578 A1 | 5/1989 |
| WO | WO-9810617 A1 | 3/1998 |
| WO | WO-0062665 A1 | 10/2000 |
| WO | WO-0108417 A1 | 2/2001 |
| WO | WO-0225773 A1 | 3/2002 |
| WO | WO-02064032 A2 | 8/2002 |
| WO | WO-02064032 A3 | 2/2003 |
| WO | WO-03015005 A2 | 2/2003 |
| WO | WO-03015838 A2 | 2/2003 |
| WO | WO-03015005 A3 | 12/2003 |
| WO | WO-2004002301 A2 | 1/2004 |
| WO | WO-03015838 A3 | 4/2004 |
| WO | WO-2004002301 A3 | 4/2004 |
| WO | WO-03015838 A9 | 5/2004 |
| WO | WO-2004084720 A2 | 10/2004 |
| WO | WO-2004084720 A3 | 3/2005 |
| WO | WO-2005029242 A2 | 3/2005 |
| WO | WO-2005029242 A3 | 6/2005 |
| WO | WO-2006094513 A2 | 9/2006 |
| WO | WO-2006094513 A3 | 4/2007 |
| WO | WO-2007101141 A2 | 9/2007 |
| WO | WO-2008035151 A2 | 3/2008 |
| WO | WO-2008097316 A1 | 8/2008 |
| WO | WO-2008035151 A3 | 12/2008 |

OTHER PUBLICATIONS

European search report and search opinion dated Apr. 16, 2014 for EP Application No. 07757453.1.
European search report dated Apr. 5, 2012 for EP Application No. 08841472.7.
International Search Report and written opinion dated Mar. 19, 2009 for PCT application No. 2008/073739.
International search report and written opinion dated Nov. 19, 2007 for PCT application No. 2007/062772.
International search report and written opinion dated Jan. 22, 2009 for PCT application No. 2008/080716.
International search report and written opinion dated Feb. 24, 2009 for PCT application No. 2008/073591.
International search report and written opinion dated Apr. 24, 2009 for PCT application No. 2008/081010.
Montemont, et al. Experimental comparison of discrete and CMOS charge sensitive preamplifiers for CZT radiation detectors. IEEE Transactions on Nuclear Science. 2002; 50(4):936-941.
Notice of allowance dated Jan. 30, 2015 for U.S. Appl. No. 12/193,865.
Notice of allowance dated Jun. 3, 2015 for U.S. Appl. No. 14/099,842.
Notice of allowance dated Aug. 16, 2013 for U.S. Appl. No. 12/739,519.
Notice of allowance dated Oct. 1, 2013 for U.S. Appl. No. 12/739,519.
Notice of allowance dated Oct. 2, 2014 for U.S. Appl. No. 12/134,151.
Notice of allowance dated Dec. 3, 2014 for U.S. Appl. No. 12/134,151.
Office action dated Feb. 12, 2013 for U.S. Appl. No. 12/739,519.
Office action dated Feb. 24, 2011 for U.S. Appl. No. 12/193,865.
Office action dated Feb. 27, 2014 for U.S. Appl. No. 12/134,151.
Office action dated Mar. 5, 2015 for U.S. Appl. No. 12/739,549.
Office action dated Mar. 29, 2012 for U.S. Appl. No. 12/739,549.
Office action dated Apr. 3, 2012 for U.S. Appl. No. 12/739,519.
Office action dated Apr. 4, 2013 for U.S. Appl. No. 12/702,127.
Office action dated Apr. 25, 2014 for U.S. Appl. No. 12/193,865.
Office action dated May 2, 2011 for U.S. Appl. No. 12/134,151.
Office action dated May 22, 2014 for U.S. Appl. No. 12/702,127.
Office action dated Jun. 19, 2014 for U.S. Appl. No. 12/096,195.
Office action dated Jun. 21, 2012 for U.S. Appl. No. 12/193,865.
Office action dated Jun. 22, 2015 for U.S. Appl. No. 12/096,195.
Office action dated Jul. 8, 2014 for U.S. Appl. No. 12/739,549.
Office action dated Jul. 9, 2013 for U.S. Appl. No. 12/096,195.
Office action dated Aug. 7, 2009 for U.S. Appl. No. 11/756,161.
Office action dated Aug. 13, 2013 for U.S. Appl. No. 12/193,865.
Office action dated Oct. 5, 2012 for U.S. Appl. No. 12/739,549.
Office action dated Nov. 6, 2014 for U.S. Appl. No. 14/099,842.
Office action dated Nov. 28, 2011 for U.S. Appl. No. 12/193,865.
Office action dated Dec. 19, 2011 for U.S. Appl. No. 12/134,151.
Uk combined search and examination report dated Jun. 26, 2012 for Application No. GB 1210339.6.
Uk combined search and examination report dated Jun. 27, 2012 for Application No. GB 1210351.1.
Uk combined search and examination report dated Sep. 12, 2011 for Application No. GB0815326.4.
Vucetic, et al. Turbo Codes: Principles and Applications. The Kluwer International Series in Engineering and Computer Science). Kluwer Academic Publishers, 2000. (Table of Contents pages only) (8 pages).
European search report and search opinion dated Nov. 23, 2015 for EP Application No. 08798285.6.
Office Action dated Jul. 28, 2016 for U.S. Appl. No. 12/096,195.
Cavalot, et al. Postprandial blood glucose is a stronger predictor of cardiovascular events than fasting blood glucose in type 2 diabetes mellitus, particularly in women: lessons from the San Luigi Gonzaga Diabetes Study. J Clin Endocrinol Metab. Mar. 2006;91(3):813-9. Epub Dec. 13, 2005.
Office Action dated Mar. 30, 2017 for U.S. Appl. No. 12/096,195.
Bailey, et al. Recommendations for standardization and specifications in automated electrocardiography: bandwidth and digital signal processing. A report for health professionals by an ad hoc writing group of the Committee on Electrocardiography and Cardiac Electrophysiology of the Council on Clinical Cardiology, American Heart Association. Circulation. Feb. 1990;81(2):730-9.
Gersten, et al. The RR interval spectrum, the ECG signal and aliasing. Eprint arXiv:physics/9911017. Nov. 1999. 17 pages.
Office Action dated Jun. 8, 2017 for U.S. Appl. No. 14/537,736.
Co-pending U.S. Appl. No. 15/836,169, filed Dec. 8, 2017.

\* cited by examiner

LOW POWER RADIOFREQUENCY (RF) COMMUNICATION SYSTEMS FOR SECURE WIRELESS PATCH INITIALIZATION AND METHODS OF USE

CROSS-REFERENCE

This application is a continuation application of U.S. patent application Ser. No. 12/739,549, filed Oct. 11, 2010, which is a continuation application of International Application No. PCT/US2008/080716, filed Oct. 22, 2008, which claims benefit of U.S. Provisional Application No. 60/982,225, filed Oct. 24, 2007, which applications are incorporated herein by reference in its entirety.

BACKGROUND OF THE INVENTION

Wireless healthcare systems are being increasingly used to help reduce healthcare cost, increase patient independence and provide better outcomes. A typical wireless healthcare system includes sensors, a host device or relay station, and a remote server. The sensors typically sense physiological signals from the body and wirelessly transmit them to a nearby host device or relay station. The host device receives the signals from the sensors and can then process and relay them to the remote server. The signal can be relayed using a cellular or other suitable type of network.

One critical aspect of remote monitoring of human physiological signals is to ensure that the privacy of the patient is maintained. Wireless transmission of these physiological signals needs to be protected against unauthorized detection of the signals. One method that can be used to ensure that patient information remains confidential includes encrypting data transmission with a 128-bit or better advanced encryption standard (AES) encryption scheme. Such a scheme involves sharing of private keys between the wireless patches and the host device prior to transmission. In order to accomplish this, sharing of private keys between the wireless patches and the host device prior to transmission can be done. This is feasible when the sensors and the host device could be purchased by patients at the same time, and also the host device could be reused with the same patch at different times. Another method is to ensure private key exchange by allowing the host device to program the keys into the sensors using near field communication so that nearby detectors cannot listen to the transmissions as the near field communication's range is only about 20 cm. Such a method can be used when it is practical to have an additional wireless method (magnetic field induction using 13.56 MHz bandwidth) that is different from the ones used by the wireless healthcare systems (radio frequency (RF) bands in the hundreds of MHz and in GHz) in the wireless patches and host device.

Therefore, a wireless healthcare system that is capable of eliminating detection of patient information by devices external to the system by operating at a low-power RF mode during the key-exchange period would be useful.

SUMMARY OF THE INVENTION

Provided herein is a wireless healthcare system comprising at least one sensor and a base unit adaptable to be in communication with the sensor in a wireless healthcare system. The sensor can be adaptable to communicate with the base unit at a first power during formation of a communication link. In some embodiments, the sensor can be in wireless communication with the base unit. The sensor can be further adaptable to communicate with the base unit at a second power after the communication link has been formed between the base unit and the sensor. The sensor can be a patch. In some embodiments, the patch can be positioned on the surface of a patient. The sensor can be adaptable to communicate with the base unit at a first power, where the first power is a low power mode. Additionally, the wireless healthcare system can comprise a sensor adaptable to sense, detect, measure, and/or monitor at least one physiological parameter from a patient. Furthermore, the wireless healthcare system can be in communication with a network server. In some embodiments, the wireless healthcare system can be in wireless communication with a network server. The wireless healthcare system can further comprise more than one sensor. The base unit can further comprise a power-amplifier. In some embodiments, the wireless healthcare system comprises a base unit wherein the base unit is adaptable to select a first power output level of −25 dBm (Decibel referenced to milliwatt) for the power amplifier and is further adaptable to attenuate the output signal by another 60 dB (Decibel). Furthermore, the base unit can further comprise an antenna. In some embodiments, the antenna can be adaptable to transmit power during the initialization phase from about −60 dBm to about −100 dBm. In some embodiments, the antenna can be adaptable to transmit power during the initialization phase of about −85 dBm. The sensor can also comprise a power-amplifier. The sensor can be adaptable to select a first power level output level of −25 dBm for the power amplifier and is further adaptable to attenuate the output signal by another 60 dB. The sensor can also comprise an antenna adaptable to transmit power during the initialization phase of about −85 dBm.

Further provided herein is a method for encrypting data sent between a base unit and at least one sensor of a wireless healthcare system comprising: bringing the at least one sensor of the wireless healthcare system proximate to the base unit of the wireless healthcare system when a communication link between base unit and the sensor is in low power mode; establishing an encrypted link between the sensor and the base unit; and increasing the power level to a higher power after the encrypted link has been formed between the sensor and the base unit. In some embodiments of the method, the wireless healthcare system comprises more than one sensor. The method can further comprise the step of establishing an encrypted link between the base and the more than one sensor. The method can further comprise transmitting patient information from the sensor to the base unit. The establishing step can further comprise selecting an initial low power level and attenuating the output level. In some embodiments of the method, the establishing step of the method can further comprise the steps of: (a) sending a beacon from the base unit to the at least one sensor to establish the communication link; (b) receiving the beacon with the at least one sensor; (c) sending a key continuously from the at least one sensor; (d) receiving the key with the base unit; (e) sending the key from the base unit to the at least one sensor; (f) receiving the key with the at least one sensor and notifying the base unit to encrypt the communication link; and (g) receiving the notification from the base unit and switching the base unit from the at least one sensor communication link to the encrypted link. The key can be selected from a phone number, retinal scan, finger print, or any other suitable biometric information, or combination thereof. The method provided herein can further comprise the step of transmitting patient information to a network server.

Further provided herein are kits for transmitting sensitive physiological data from a patient to a host device comprising at least one sensor adaptable to be positioned on a patient and a base unit in communication with the at least one sensor, wherein the sensor is adaptable to communicate with the base unit at a first power during formation of a communication link and is further adaptable to communicate with the base unit at a second power after the communication link has been formed, and wherein the sensor and base unit are components of a wireless healthcare system. The kit can comprise more than one sensor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
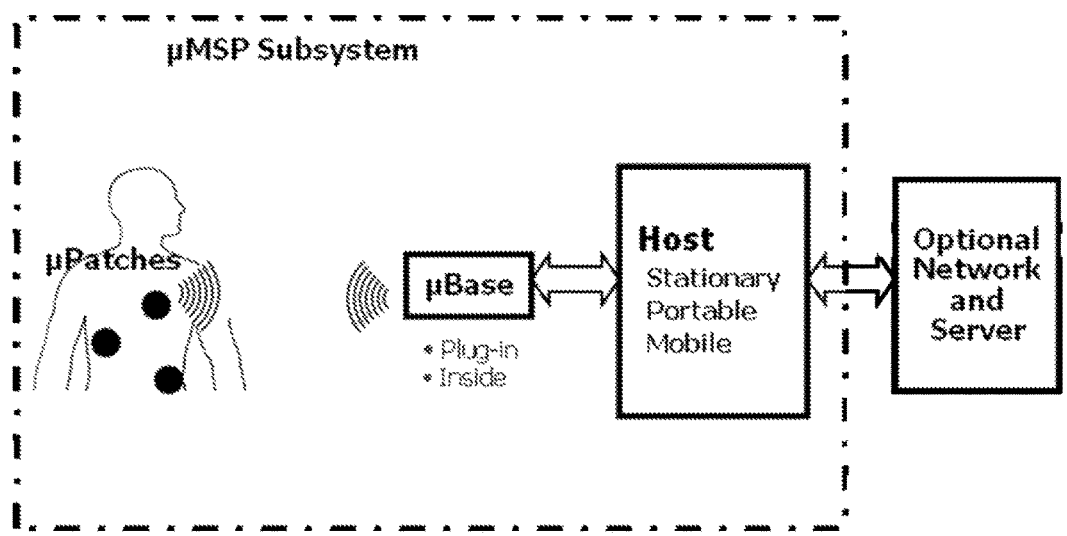
FIG. 1 illustrates one embodiment of a wireless healthcare system.

Provided herein is a wireless healthcare system comprising at least one sensor and a base unit adaptable to be in communication with the sensor in a wireless healthcare system. The sensor can be adaptable to communicate with the base unit at a first power during formation of a communication link. In some embodiments, the sensor can be in wireless communication with the base unit. The sensor can be further adaptable to communicate with the base unit at a second power after the communication link has been formed between the base unit and the sensor. The sensor can be a patch. In some embodiments, the patch can be positioned on the surface of a patient. The sensor can be a wearable garment wearable by the patient that can detect signals from the patient. The sensor can be adaptable to communicate with the base unit at a first power, where the first power is a low power mode. Additionally, the wireless healthcare system can comprise a sensor adaptable to sense, detect, measure, and/or monitor at least one physiological parameter from a patient. Furthermore, the wireless healthcare system can be in communication with a network server. In some embodiments, the wireless healthcare system can be in wireless communication with a network server. The wireless healthcare system can further comprise more than one sensor. The base unit can further comprise a power-amplifier. In some embodiments, the wireless healthcare system comprises a base unit wherein the base unit is adaptable to select a first power output level of −25 dBm for the power amplifier and is further adaptable to attenuate the output signal by another 60 dB. Furthermore, the base unit can further comprise an antenna. In some embodiments, the antenna can be adaptable to transmit power during the initialization phase from about −60 dBm to about −100 dBm. In some embodiments, the antenna can be adaptable to transmit power during the initialization phase of about −85 dBm. The sensor can also comprise a power-amplifier. The sensor can be adaptable to select a first power level output level of −25 dBm for the power amplifier and is further adaptable to attenuate the output signal by another 60 dB. The sensor can also comprise an antenna adaptable to transmit power during the initialization phase of about −85 dBm.

I. Systems

Provided herein is a wireless healthcare system for use in transmitting patient information in a secure fashion using a wireless communication device. The device provided herein includes a sensor for transmitting a signal to a base unit using a key-exchange program to encrypt the signal, thereby preventing devices external to the system, but in range of the signal, from detecting the signal transmitted between the sensor and the base unit. For a wireless healthcare system to be used for private key exchange, the radio radiofrequency (RF) power of the base unit transmitter needs to be reduced close to the sensitivity of the wireless sensor receiver so that the transmitter and receiver could be brought close to each other and still maintain a wireless link. An additional external electrical device not part of the system but capable of detecting the electrical signal between the sensor and base unit, or eavesdropping, positioned one meter away from the system will only detect a signal significantly below the receiver sensitivity. For example purposes only, an external device near the system described herein will detect a signal with at least a 40 dB of free space loss, making reception by the external device nearly impossible.

In some embodiments, the initial placement of the patches on the human body is followed by a wireless initialization sequence at very low power by bringing the base unit and the sensor in proximity to each other. Normal data transmission of a signal from the sensors from the sensors to the base unit can then occur following the initialization at normal power-level and range of operation. This ability to bring the sensors and the base unit close to each other distinguishes the wireless healthcare system from a generic wireless network where bringing the sensor and the base unit in close proximity might not be possible. The ability to bring the sensor and base unit close together can simplify the complexity and operation of the system, and can reduce the cost of the system.

FIG. 1 illustrates one embodiment of a wireless healthcare system. The wireless healthcare system can comprise at least one sensor and a base unit. In some embodiments, multiple sensors are used. The sensor can be positioned on a patient as shown in FIG. 1. The sensor can be a wireless sensor. Alternatively, the sensor can be in the form of a patch. Alternatively, the sensor can be in the form of a wearable garment. The sensor can be a wired sensor, where the sensor is wired to a base unit. In some embodiments, the sensor can be a wireless sensor in wireless communication with the base unit. When the sensor is ready for use, the sensor can be powered up. During the power up processes, the sensor undergoes a boot-up process. During this time, an attempt can be made to form a connection between the sensor and the base unit. The sensor can wait to receive commands from the base unit to establish wireless link parameters to transmit data. In order to establish a wireless link, the sensor either listens in a predetermined "broadcast channel" or alternatively, the sensor can scan multiple channels where the host device may be transmitting beacons for the sensor. In some embodiments, the sensor itself could give an indication that the sensor is ready to be initialized. The patch or wearable item could also give an indication that the sensor is ready to be initialized. The sensor can give an audio indication that the sensor is ready to be initialized. Alternatively, the sensor can give a visual indication that the sensor is ready to be initialized.

Figure 2:
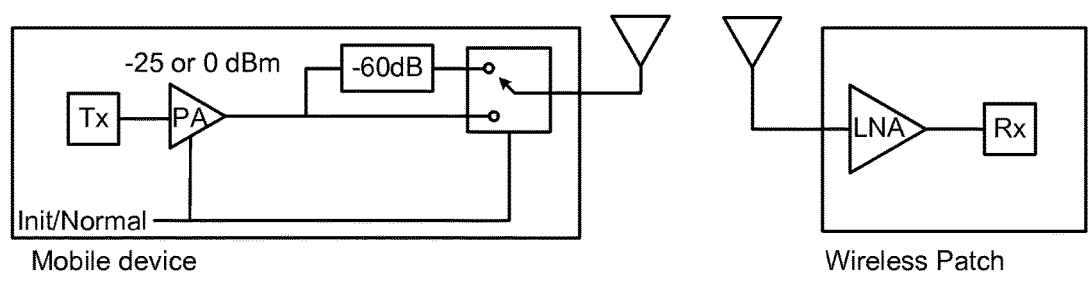
FIG. 2 illustrates the components of one embodiment of a low power-RF transmitter and one embodiment of a receiver.

The base unit can be a component of a host system. Alternatively the base unit can be a stand alone unit in communication with the sensor. FIG. 2 illustrates one embodiment of a sensor and base unit. The sensor in FIG. 2 has a sensitivity of −90 dBm. A receiver signal strength of −85 dBm is assumed to result in virtually error-free data reception during the initialization process. Any suitable signal and sensitivity level that results in error-free operation can be used.

Once the sensor has given an indication that the sensor is ready to be initialized, the end-user can then start the initialization process by bringing the base unit close to the wireless sensor. Alternatively, the wireless sensor can be brought close to the base unit. The sensor can be positioned within about 15 cm of the base unit. Additionally, the sensor can be positioned within about 10 cm of the base unit. The sensor can be positioned within about 5 cm of the base unit. In some embodiments, the sensor can be positioned within about 2 cm of the base unit.

The initialization process can then be started by the end-user. The base unit can select a low initialization power level of −25 dBm for the internal/external power-amplifier (PA) to send commands to the wireless patch to be initiated. The base unit can then further attenuate the output signal by another 60 dB by switching to an RF path that includes a 60 dB attenuator. This results in a −85 dBm radiated power at the transmit antenna. In some embodiments, the power radiated from antenna can range between about −60 dBm and −100 dBm. The close proximity of the sensor to the base unit can allow the sensor to receive the signal from the base unit reliably. The sensor can also verify that the signal is received error-free. In some embodiments, the signal can be checked for alteration using a cyclic redundancy check (CRC) of the received data packet. The sensor can then compare the signal after the CRC to the signal at the beginning of the initialization sequence. If the CRC fails, the sensor can ignore the signal from the base unit. No connection between the base unit and the sensor is formed and the sensor stays in listening mode.

The system provided herein can be a static system that establishes a link between the base and the sensor at one distance using one lower power. In some embodiments, the system can comprise a system that can be adjusted. For example, in some cases a higher complexity eavesdropping receiver with extremely low sensitivity can be in proximity to the system wherein the eavesdropping receiver can detect and demodulate transmissions at power as low as −185 dBm. The system could then lower the power transmission level to a lower level. Additionally, the base unit can be brought into closer proximity to the sensor. Using an even lower power level but having the sensor and base unit in closer proximity can help to maintain a reliable wireless link between the base unit and sensor at such low power levels.

Provided herein is one embodiment of a key-exchange program for sending encrypted data in order to establish a connection between the sensor and the base unit. The key-exchange program can comprise the base unit continuously sending out a beacon to be detected by the sensor. The wireless sensor can receive the beacon from the base unit, thereby establishing a preliminary connection between the base unit and the sensor. The sensor can then send out a key (information or a parameter that determines the functional output of a cryptic algorithm) continuously to the base unit. The base unit then receives the key from the sensor and then sends the key continuously back to the sensor. After receiving the key, the sensor sends continuous notification to the base unit that it is permissible to switch to the encrypted channel. The sensor then listens for a signal from the base unit on the encrypted channel. The base unit can then receive the switching message from the sensor and switches to the encrypted channel. In some embodiments, the wireless sensor can send acknowledgments or other capability parameter messages to the base unit using a similar low-power mode for transmission to the host device. Together, the host device and the wireless patch can exchange encryption key information at power levels not detectable by eavesdroppers or other external devices that are within range and are of similar setup.

After the key-exchange between the sensor and the base unit is complete, the sensor and base unit can communicate reliably with each other to establish and complete the initialization process. Any signal received by an eavesdropping device at this point suffers an additional 40 dB free-space path-loss (−135 dBm) or more, even at one meter distances from the base unit. This reduction in free-space path-loss can make it virtually impossible for an eavesdropping device to detect and demodulate the transmission signal between the sensor and the base-unit. Any similar signal attenuation mechanism can be used to achieve low-power transmissions. For example purposes only, different combinations of power amplified power and one or more attenuator stages could be used to achieve the desired power level. The initialization sequence can also be modified to follow near field communication (NFC) Forum's technical specifications. In some embodiments, an NFC transceiver can be employed in addition to a radiofrequency (RF) transceiver which would use the same RF antenna. In this case, the RF antenna tuned for RF frequencies can provide the adequate attenuation at the NFC frequency providing the desired privacy.

Additionally, any subsequent (periodic) key exchange for enhanced privacy does not need to involve low-power transmissions, as they can use the existing keys to encrypt the transmitted data containing the new keys. The key can also be the unique identification of the end-user including, but not limited to, the end user's mobile phone number, or any suitable biometric information such as finger-print, or retinal scan.

In some embodiments, multiple sensors can be used. The same authentication key can be used by the base unit in conjunction with multiple sensors that are in close proximity to each other. By issuing a single command on the host device, the end user needs to initiate the authentication process once. The base unit can then go through the above procedure with each wireless patch to authenticate all of the remaining sensors. This eliminates the need to authenticate all the sensors separately.

Once the initialization is completed successfully, subsequent transmissions between the base unit and the sensor can be encrypted. The transmit power levels are restored to normal levels by switching to higher power-levels of the power-amplifier, as well as bypassing the RF path with the 60 dB attenuation.

In some embodiments, the system can be adaptable to upload information from the base unit onto a network server.

The base unit can be hard-wired to the network server. Alternatively the base unit can be wirelessly connected to the network server.

II. Methods

Further provided herein is a method for encrypting data sent between a base unit and at least one sensor of a wireless healthcare system comprising: bringing the at least one sensor of the wireless healthcare system proximate to the base unit of the wireless healthcare system when a communication link between base unit and the sensor is in low power mode; establishing an encrypted link between the sensor and the base unit; and increasing the power level to a higher power after the encrypted link has been formed between the sensor and the base unit. In some embodiments of the method, the wireless healthcare system comprises more than one sensor. The method can further comprise the step of establishing an encrypted link between the base and the more than sensor. The method can further comprise transmitting patient information from the sensor to the base unit. The establishing step can further comprise selecting an initial low power level and attenuating the output level. In some embodiments of the method, the establishing step of the method can further comprise the steps of: (a) sending a beacon from the base unit to the at least one sensor to establish the communication link; (b) receiving the beacon with the at least one sensor; (c) sending a key continuously from the at least one sensor; (d) receiving the key with the base unit; (e) sending the key from the base unit to the at least one sensor; (f) receiving the key with the at least one sensor and notifying the base unit to encrypt the communication link; and (g) receiving the notification from the base unit and switching the base unit from the at least one sensor communication link to the encrypted link. The key can be selected from a phone number, retinal scan, finger print, or any other suitable biometric information, or combination thereof. The method provided herein can further comprise the step of transmitting patient information to a network server.

III. Kits

Further provided herein are kits for transmitting sensitive physiological data from a patient to a host device comprising: at least one sensor adaptable to be positioned on a patient; and a base unit in communication with the at least one sensor, wherein the sensor is adaptable to communicate with the base unit at a first power during formation of a communication link and is further adaptable to communicate with the base unit at a second power after the communication link has been formed, and wherein the sensor and base unit are components of a wireless healthcare system. The kit can comprise more than one sensor.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A wireless healthcare system comprising:
   at least one sensor configured to be positioned on a surface of a user, wherein the sensor comprises a first power amplifier and a first set of one or more attenuators, and wherein the sensor is adaptable to select a first power mode for the first power amplifier and the first set of one or more attenuators is adaptable to further attenuate an output signal at a first power level from the first power amplifier to generate a signal at a second power level, wherein the second power level is lower than the first power level; and
   a base unit adaptable to be in direct wireless communication with the sensor via a communication link, wherein the base unit comprises a second power amplifier and a second set of one or more attenuators, and wherein the base unit is adaptable to select the first power mode for the second power amplifier and the second set of one or more attenuators is adaptable to further attenuate an output signal from the second power amplifier,
   wherein the sensor is adaptable to 1) be in direct wireless communication with the base unit via the communication link, 2) operate at the first power level in forming the communication link between the sensor and the base unit, 3) operate at the second power level in forming the communication link between the sensor and the base unit, and 4) operate at a third power level different from the first power level and the second power level to communicate with the base unit via the communication link between the sensor and the base unit after the communication link has been formed and established as an encrypted link, and wherein the sensor and base unit are components of a wireless healthcare system.

2. The wireless healthcare system of claim 1 wherein the sensor is a patch adaptable to be positioned on a surface of a patient.

3. The wireless healthcare system of claim 1 wherein the sensor is adaptable to detect at least one physiological parameter from a patient.

4. The wireless healthcare system of claim 1 wherein the base unit is further adaptable to be in external communication with a network server.

5. The wireless healthcare system of claim 1 further comprising more than one sensor.

6. The wireless healthcare system of claim 1 wherein the base unit further comprises an antenna.

7. The wireless healthcare system of claim 6 wherein the antenna is adaptable to transmit power during an initialization phase of −85 decibel-milliwatts (dBm).

8. The wireless healthcare system of claim 1 wherein the sensor further comprises an antenna.

9. The wireless healthcare system of claim 8 wherein the antenna is adaptable to transmit power during an initialization phase of −85 dBm.

10. The wireless healthcare system of claim 1, wherein the sensor is configured to give an indication that the sensor is ready to be initialized with the base unit.

11. The wireless healthcare system of claim 1, wherein the sensor is configured to verify that a signal received from the base unit is error-free by checking for alteration using a cyclic redundancy check (CRC) of received data packets.

12. The system of claim 1, wherein the first set of one or more attenuators and the second set of one or more attenuators are adjustable to attenuate signals during formation of the communication link based on a desired power level.

13. The system of claim 1, wherein the sensor is adaptable to initially operate at the first power level in forming the communication link between the sensor and the base unit, and, upon detection of an eavesdropping receiver, attenuate the first power level to the second power level and operate at the second power level to form the communication link between the sensor and the base unit.

14. A method for encrypting data sent between a base unit and at least one sensor of a wireless healthcare system comprising:
(a) bringing the at least one sensor of the wireless healthcare system to a predetermined distance threshold of the base unit of the wireless healthcare system, wherein the at least one sensor is configured to be positioned on a surface of a user, wherein each of the base unit and the at least one sensor comprise a power amplifier and a set of one or more attenuators, and wherein each of the base unit and the at least one sensor is adaptable to select a first power mode for the power amplifier and the set of one or more attenuators is adaptable to further attenuate an output signal at a first power level from the power amplifier to generate a signal at a second power level, wherein the second power level is lower than the first power level;
(b) initiating direct wireless communication between the at least one sensor and the base unit via a communication link when each of the base unit and the at least one sensor at the first power level or the second power level;
(c) establishing an encrypted link as the communication link between the sensor and the base unit; and
(d) increasing a power level of the sensor from the first power level or the second power level to a higher power level, that is greater than the first power level and the second level, after the encrypted link has been established between the at least one sensor and the base unit.

15. The method of claim 14 further comprising transmitting patient information from the sensor to the base unit.

16. The method of claim 14 wherein the establishing comprises selecting an initial low power level and attenuating the output level.

17. The method of claim 14 wherein the establishing step further comprises:
(e) sending a beacon from the base unit to the at least one sensor to establish a communication channel;
(f) receiving the beacon with the at least one sensor;
(g) sending a key continuously from the at least one sensor;
(h) receiving the key with the base unit;
(i) sending the key from the base unit to the at least one sensor;
(j) receiving the key with the at least one sensor and notifying the base unit to encrypt the communication channel; and
(k) receiving the notification from the base unit and switching the communication link between the base unit and the at least one sensor to the encrypted link formed by encrypting the communication channel.

18. The method of claim 17 wherein the key is selected from at least one of a phone number, retinal scan, fingerprint, or biometric information.

19. The method of claim 17 further comprising transmitting patient information to a network server.

20. The method of claim 14, wherein the encrypted link is established within the predetermined distance threshold.

21. The method of claim 14, wherein the predetermined distance threshold is 15 centimeters (cm).

22. A system for transmitting sensitive physiological data from a patient to a host device comprising:
(a) at least one sensor adaptable to be positioned on a surface of a patient, wherein the sensor comprises a first power amplifier and a first set of one or more attenuators, and wherein the sensor is adaptable to select a first power mode for the first power amplifier and the first set of one or more attenuators is adaptable to further attenuate an output signal at a first power level from the first power amplifier to generate a signal at a second power level, wherein the second power level is lower than the first power level; and
(b) a base unit in direct wireless communication with the at least one sensor via a communication link, wherein the base unit comprises a second power amplifier and a second set of one or more attenuators, and wherein the base unit is adaptable to select the first power mode for the second power amplifier and the second set of one or more attenuators is adaptable to further attenuate an output signal from the second power amplifier,
wherein the sensor is adaptable to 1) be in direct wireless communication with the base unit via the communication link, 2) operate at the first power level in forming the communication link between the sensor and the base unit, 3) operate at the second power level in forming the communication link between the sensor and the base unit, and 4) operate at a third power level different from the first power level and the second power level to communicate with the base unit via the communication link between the sensor and the base unit after the communication link has been formed and established as an encrypted link, and wherein the sensor and base unit are components of a wireless healthcare system.

23. The system of claim 22 further comprising more than one sensor.

* * * * *